(12) United States Patent
Shimoda et al.

(10) Patent No.: US 8,647,876 B2
(45) Date of Patent: Feb. 11, 2014

(54) OXYGEN PERMEABILITY MEASURING APPARATUS AND METHOD, AND DEFECT INSPECTION APPARATUS AND METHOD

(75) Inventors: Tomoyuki Shimoda, Kanagawa (JP);
Yoshio Inagaki, Kanagawa (JP);
Kimiaki Miyamoto, Kanagawa (JP)

(73) Assignee: Fujifilm Corporation, Tokyo (JP)

( * ) Notice: Subject to any disclaimer, the term of this patent is extended or adjusted under 35 U.S.C. 154(b) by 397 days.

(21) Appl. No.: 13/077,226

(22) Filed: Mar. 31, 2011

(65) Prior Publication Data
US 2011/0244577 A1  Oct. 6, 2011

(30) Foreign Application Priority Data

Mar. 31, 2010  (JP) ................................. 2010-080277
Mar. 31, 2010  (JP) ................................. 2010-080278

(51) Int. Cl.
| | |
|---|---|
| *G01N 21/90* | (2006.01) |
| *G01N 21/88* | (2006.01) |
| *G01N 21/73* | (2006.01) |
| *G01N 21/01* | (2006.01) |
| *G01N 31/22* | (2006.01) |

(52) U.S. Cl.
USPC .......... 436/1; 422/52; 436/3; 436/5; 436/127; 436/136; 436/138; 436/172

(58) Field of Classification Search
USPC ......... 422/52; 436/1, 3, 5, 127, 136, 138, 172
See application file for complete search history.

(56) References Cited

U.S. PATENT DOCUMENTS

| | | | | |
|---|---|---|---|---|
| 3,239,519 A | * | 3/1966 | Winberg ......................... | 544/78 |
| 3,301,043 A | * | 1/1967 | Lyssy ............................. | 73/38 |
| 3,498,110 A | * | 3/1970 | Brun ................................ | 73/38 |
| 3,502,588 A | * | 3/1970 | Winberg ....................... | 252/700 |
| 3,555,884 A | * | 1/1971 | Yamamoto et al. ............. | 73/40.7 |
| 3,572,096 A | * | 3/1971 | Meyer ............................ | 73/40.7 |
| 3,590,634 A | * | 7/1971 | Pasternak et al. ............... | 374/54 |
| 3,604,246 A | * | 9/1971 | Toren ................................ | 73/38 |
| 3,669,891 A | * | 6/1972 | Greenwood et al. ......... | 424/10.1 |

(Continued)

FOREIGN PATENT DOCUMENTS

| | | |
|---|---|---|
| JP | 54-111390 | 8/1979 |
| JP | 54-130091 | 10/1979 |

(Continued)

OTHER PUBLICATIONS

Freeman, T. M, et al, Analytical Chemistry 1981, 53, 98-102.*

(Continued)

*Primary Examiner* — Arlen Soderquist
(74) *Attorney, Agent, or Firm* — Young & Thompson

(57) ABSTRACT

An oxygen permeability measuring apparatus for measuring an oxygen permeation rate of oxygen barrier film in a dark room is provided. A container is charged with inert gas, and sealed hermetically by use of the oxygen barrier film at least partially. A chemiluminescent compound is contained in the container, for emitting light by oxidation with the oxygen. A photon detector detects photons emitted by the chemiluminescent compound so as to determine an amount of the oxygen permeated through the oxygen barrier film. Preferably, the container includes a container body. An opening is formed in the container body, and closed hermetically by the oxygen barrier film attached thereto. The photon detector is disposed inside or outside the container. The oxygen permeation rate is equal to or less than $10^{-2}$ cc/m$^2$·day·atm. The chemiluminescent compound includes tetrakis(dimethylamino)ethylene.

25 Claims, 14 Drawing Sheets

(56) References Cited

U.S. PATENT DOCUMENTS

| | | | |
|---|---|---|---|
| 3,902,068 A * | 8/1975 | Wood | 250/343 |
| 4,464,927 A * | 8/1984 | Reid | 73/38 |
| 4,468,951 A * | 9/1984 | Garcia et al. | 73/38 |
| 4,476,870 A * | 10/1984 | Peterson et al. | 600/312 |
| RE31,879 E * | 5/1985 | Lubbers et al. | 436/133 |
| 4,656,865 A * | 4/1987 | Callan | 73/38 |
| 4,968,892 A * | 11/1990 | McAtee | 250/458.1 |
| 5,015,856 A * | 5/1991 | Gold | 250/339.09 |
| 5,107,696 A * | 4/1992 | Mayer et al. | 73/38 |
| 5,316,949 A * | 5/1994 | Bull et al. | 436/5 |
| 5,381,228 A * | 1/1995 | Brace | 356/300 |
| 5,407,829 A * | 4/1995 | Wolfbeis et al. | 436/1 |
| 5,439,648 A * | 8/1995 | Balderson et al. | 422/86 |
| 5,445,795 A * | 8/1995 | Lancaster et al. | 422/86 |
| 5,458,896 A * | 10/1995 | Porter | 426/232 |
| 5,483,819 A * | 1/1996 | Barmore et al. | 73/38 |
| 5,513,515 A * | 5/1996 | Mayer | 73/38 |
| 5,583,047 A * | 12/1996 | Blinka et al. | 436/5 |
| 5,591,898 A * | 1/1997 | Mayer | 73/38 |
| 5,593,899 A * | 1/1997 | Wilson et al. | 436/127 |
| 5,617,812 A * | 4/1997 | Balderson et al. | 116/206 |
| 5,792,940 A * | 8/1998 | Ghandhi | 73/40 |
| 5,837,888 A * | 11/1998 | Mayer et al. | 73/38 |
| 5,863,460 A * | 1/1999 | Slovacek et al. | 252/301.35 |
| 6,050,133 A * | 4/2000 | Achter et al. | 73/40.7 |
| 6,138,497 A * | 10/2000 | Nix et al. | 73/19.06 |
| 6,325,974 B1 * | 12/2001 | Ahvenainen et al. | 422/416 |
| 6,335,202 B1 * | 1/2002 | Lee et al. | 436/161 |
| 6,345,191 B1 * | 2/2002 | Hartmann et al. | 600/310 |
| 6,399,387 B1 * | 6/2002 | Stenholm et al. | 436/1 |
| 6,479,018 B2 * | 11/2002 | Collins et al. | 422/83 |
| 6,513,366 B1 * | 2/2003 | Stauffer | 73/49.3 |
| 6,561,008 B1 * | 5/2003 | Mulholland et al. | 73/38 |
| 6,640,615 B1 * | 11/2003 | Morrow | 73/38 |
| 6,652,810 B1 * | 11/2003 | Ziegler | 422/82.08 |
| 6,689,438 B2 * | 2/2004 | Kennedy et al. | 428/36.6 |
| 7,112,443 B2 * | 9/2006 | Hajduk et al. | 436/5 |
| 7,121,135 B2 * | 10/2006 | Moore | 73/38 |
| 7,219,799 B2 * | 5/2007 | Bonnette et al. | 206/459.1 |
| 7,368,153 B2 * | 5/2008 | Barmore et al. | 428/36.7 |
| 7,534,615 B2 * | 5/2009 | Havens | 436/3 |
| 7,569,395 B2 * | 8/2009 | Havens et al. | 436/172 |
| 7,624,622 B1 * | 12/2009 | Mayer et al. | 73/38 |
| 7,781,221 B2 * | 8/2010 | Mueller | 436/127 |
| 8,015,857 B2 * | 9/2011 | Piombini et al. | 73/38 |
| 8,117,899 B2 * | 2/2012 | Piombini et al. | 73/38 |
| 8,158,077 B2 * | 4/2012 | Kanehara et al. | 422/400 |
| 8,424,367 B2 * | 4/2013 | Ploehn et al. | 73/38 |
| 8,450,113 B2 * | 5/2013 | Lupke et al. | 436/5 |
| 8,505,361 B2 * | 8/2013 | Miller et al. | 73/49.3 |
| 2002/0162384 A1 * | 11/2002 | Sharp et al. | 73/38 |
| 2002/0194899 A1 * | 12/2002 | Gebele et al. | 73/38 |
| 2004/0012775 A1 * | 1/2004 | Kinney et al. | 356/237.2 |
| 2004/0040372 A1 * | 3/2004 | Plester et al. | 73/38 |
| 2004/0077091 A1 * | 4/2004 | Hajduk et al. | 436/5 |
| 2007/0212789 A1 * | 9/2007 | Havens et al. | 436/138 |
| 2007/0296963 A1 * | 12/2007 | Parker et al. | 356/240.1 |
| 2009/0236542 A1 * | 9/2009 | Wallis | 250/459.1 |

FOREIGN PATENT DOCUMENTS

| | | |
|---|---|---|
| JP | 63-133039 | 6/1988 |
| JP | 02-051043 | 2/1990 |
| JP | 2007-010382 | 1/2007 |
| WO | 03031952 | 4/2003 |
| WO | 2007/106778 | 9/2007 |

OTHER PUBLICATIONS

Yekta, A. et al, Canadian Journal of Chemistry 1995, 73, 2021-2029.*
Rharbi, Y. et al, Analytical Chemistry 1999, 71, 5045-5053.*
Celina, M. et al, Macromolecules 2005, 38, 2754-2763.*

* cited by examiner

F I G. 6
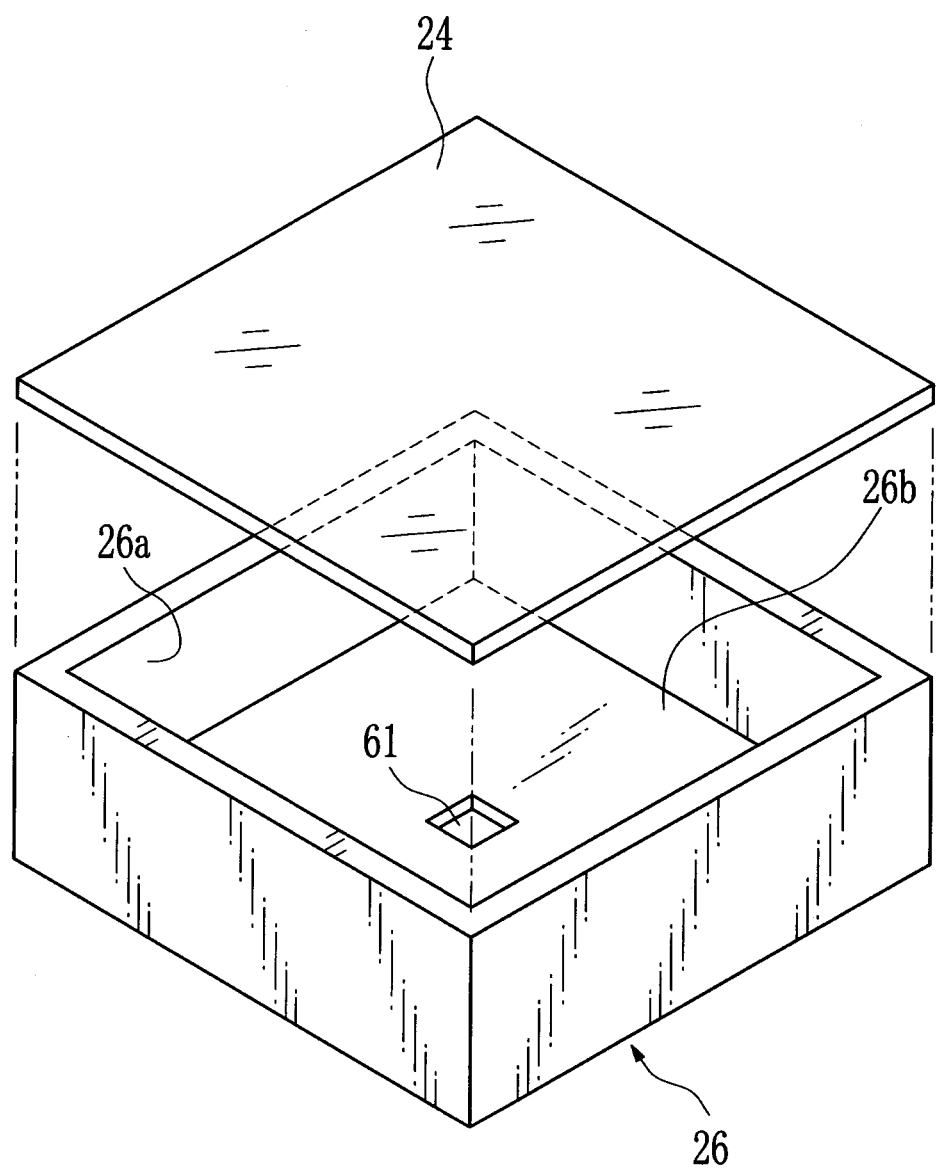

OXYGEN PERMEABILITY MEASURING APPARATUS AND METHOD, AND DEFECT INSPECTION APPARATUS AND METHOD

BACKGROUND OF THE INVENTION

1. Field of the Invention

The present invention relates to an oxygen permeability measuring apparatus and method, and defect inspection apparatus and method. More particularly, the present invention relates to an oxygen permeability measuring apparatus and method, and defect inspection apparatus and method, which is capable of measuring or inspecting oxygen permeability even for a very small oxygen amount.

2. Description Related to the Prior Art

Quality of food and/or drugs will drop when oxidation occurs. It is well-known to use an oxygen barrier material for packaging the food with a small value of an oxygen permeation rate, for example, $10^{-2}$ cc/m$^2$·day·atm. Thus, the food is packaged by use of an oxygen barrier film formed from the oxygen barrier material, or a container formed from the oxygen barrier material as an oxygen barrier container.

Examples of known methods of measuring the oxygen permeation rate of the oxygen barrier material are a differential pressure method and equal pressure method (JIS K 7126). According to those, a chamber is split into two areas by use of the oxygen barrier material as a sample material of the measurement. In the first area, oxygen is introduced. In the second area, oxygen permeated through the sample material is monitored by use of a pressure sensor. Furthermore, JP-A 54-130091 discloses a method in which the sample material is formed in a bag shape. Inert gas is filled in the sample material which is left to stand in the atmosphere. Let the first area be an outer area of the atmosphere. Let the second area be the inside of the bag. When a predetermined time elapses, an oxygen amount in the second area is measured by an analyzer, so as to measure the oxygen permeation rate of the sample material.

Also, JP-A 54-111390 and JP-A 2007-010382 disclose a detection method of detecting presence of a defect in the oxygen barrier material, or a portion where oxygen is easy to permeate. In the detection, the container is filled with a substance of developing color upon occurrence of the oxidation or reduction. The container is exposed to the atmosphere having oxygen, for example the atmospheric air. The defect of the container can be discovered according to a position of a colored portion of the substance.

New attempts are made today for producing an optical device and electronic device by use of a substrate of an organic film in contrast with the well-known use of an inorganic substrate. This will make it possible to lower the cost of the substrate, reduce the thickness, and raise the flexibility. Recent needs for enlargement of products and wearable products may be satisfied when the organic film is used.

Various requirements occur with a new use of the organic film for a substrate of the electronic device. A problem lies in an oxygen barrier property of the organic film. If the organic film has only a low value of the oxygen barrier property, the electronic device may be broken by oxygen transmitted through the organic film. Accordingly, the oxygen barrier film is required between the organic film and the electronic device. Furthermore, the electronic device must be covered with the oxygen barrier film. The oxygen permeation rate of the SiNx film used presently for protecting the electronic device is approximately $10^{-2}$ cc/m$^2$·day·atm. However, in view of environmental compatibility of the electronic device, it will be necessary for a protection film to have the oxygen barrier property at a level of the oxygen permeation rate of $10^{-4}$ cc/m$^2$·day·atm for a solar cell, and $10^{-6}$ cc/m$^2$·day·atm for an inorganic EL element. Those types of the oxygen barrier material will have such a high performance that a conventional technique of evaluation cannot evaluate. No method of precise evaluation of the performance of the oxygen barrier material has been known.

The oxygen permeation rate of a very low level is required also for an organic EL element for use in an organic EL display panel, oxygen barrier film for a solar cell, oxygen barrier film for electronic paper, and the like.

A serious problem lies in the method of JP-A 54-130091 for evaluating the performance of the oxygen barrier material. Very longtime will be required for acquiring sufficient oxygen density for the measurement, because of a rate determining value of the detecting performance of the pressure sensor. According to the disclosed information, the measurement is conducted for 30 days in a range of 0.8-44.7 cc/m$^2$·day·atm. JP-A 54-111390 and JP-A 2007-010382 disclose a method of estimating the oxygen permeation rate by use of leuco methylene blue as a color developer for coloring upon the oxidation. In the method, the container of a normal shape is prepared. A needle with a diameter of 0.2 mm is thrust in the container at a depth of 0.05 mm so that a hole is formed as a portion of a reduced thickness. The portion of the hole has a smaller oxygen barrier property than the remaining portion with a normal thickness. A component of the leuco methylene blue disposed behind the hole develops blue color, which indicates a drop of the oxygen barrier property. However, there arises a problem in the method in that the oxygen barrier property at the hole cannot be quantified for evaluation even after detection of the hole. Also, an apparatus for delivery of gas is required and will excessively enlarge the entire size of the system according to the method determined in the JIS (Japanese Industrial Standards).

SUMMARY OF THE INVENTION

In view of the foregoing problems, an object of the present invention is to provide an oxygen permeability measuring apparatus and method, and defect inspection apparatus and method, which is capable of measuring or inspecting oxygen permeability even for a very small oxygen amount.

In order to achieve the above and other objects and advantages of this invention, an oxygen permeability measuring apparatus for measuring an oxygen permeation rate of oxygen barrier film is provided. A container is disposed in a dark room, charged with inert gas, and sealed hermetically by use of the oxygen barrier film at least partially. A chemiluminescent compound is contained in the container, for emitting light by oxidation with oxygen. A photon detector detects photons emitted by the chemiluminescent compound so as to determine an amount of the oxygen permeated through the oxygen barrier film into the container.

The container includes a container body. An opening is formed in the container body, and closed hermetically by the oxygen barrier film.

In one preferred embodiment, the container is a container bag constituted by the oxygen barrier film.

The photon detector is disposed inside or outside the container.

The oxygen permeation rate is equal to or less than $10^{-2}$ cc/m$^2$·day·atm.

The chemiluminescent compound includes a compound according to a formula of:

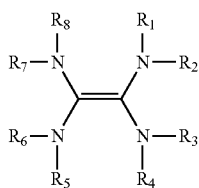

where R1-R8 denote alkyl groups identical to or different from each other.

The chemiluminescent compound includes tetrakis(dimethylamino)ethylene.

The photon detector includes a photomultiplier tube.

Also, an oxygen permeability measuring method includes a step of containing a chemiluminescent compound in a container charged with inert gas, the chemiluminescent compound emitting light by oxidation with oxygen. Oxygen-containing gas is permeated through oxygen barrier film. The permeated oxygen-containing gas is provided to contact the chemiluminescent compound in the container in a dark room. Photons emitted by the chemiluminescent compound are detected. An amount of the oxygen permeated through the oxygen barrier film is determined according to an amount of the photons.

Furthermore, before the permeating step, the container is hermetically sealed by use of the oxygen barrier film at least partially.

The container includes a container body. An opening is formed in the container body, and closed hermetically by the oxygen barrier film attached thereto.

In one preferred embodiment, the container is an oxygen barrier container constituted by forming the oxygen barrier film in a bag shape.

In another preferred embodiment, furthermore, before the permeating step, a gas container is hermetically sealed with the oxygen barrier film in charging the gas container with inert gas. After the permeating step, the permeated oxygen-containing gas is drawn from the gas container to introduce the permeated oxygen-containing gas into the container.

Also, a defect inspection apparatus for an oxygen barrier material includes a hermetic container disposed in a dark room, and constituted by the oxygen barrier material at least partially. A chemiluminescent compound is contained in the container, for emitting light by oxidation with oxygen. A photon counter detects a number M of photons emitted by the chemiluminescent compound. A comparison unit checks whether the number M is more than a threshold N. A determining device determines a detection position of the photon counter upon detecting the number M if the comparison unit determines that M>N.

Furthermore, a moving device moves the photon counter along the oxygen barrier material.

In one preferred embodiment, the photon counter is constituted by plural photon counters arranged in a photon counter array.

The photon counter array extends along a surface of the oxygen barrier material.

In one preferred embodiment, furthermore, there is a condensing lens for light condensing of the photons emitted by the chemiluminescent compound to the photon counter.

The oxygen barrier material tightly contacts the chemiluminescent compound, and seals the chemiluminescent compound in the container.

The container includes a container body. An opening is formed in the container body, and closed hermetically by the oxygen barrier material attached thereto.

The chemiluminescent compound includes tetrakis(dimethylamino)ethylene.

The photon counter includes a photomultiplier tube.

Also, a defect inspection method for an oxygen barrier material includes a step of containing a chemiluminescent compound in a hermetic container for emitting light by oxidation with oxygen, the container being constituted by the oxygen barrier material at least partially. The container is exposed in presence of the oxygen in a dark room with the chemiluminescent compound contained therein. The exposing step includes detecting a number M of photons emitted by the chemiluminescent compound by use of a photon counter contained in the container. It is checked whether the number M is more than a threshold N. A detection position of the photon counter is determined upon detecting the number M if M>N.

In the exposing step, the photon counter is moved along the oxygen barrier material.

Accordingly, it is possible to measure or inspect oxygen permeability even for a very small oxygen amount, because the photon detector is used in combination with the chemiluminescent compound.

BRIEF DESCRIPTION OF THE DRAWINGS

The above objects and advantages of the present invention will become more apparent from the following detailed description when read in connection with the accompanying drawings, in which:

FIG. 6 is a perspective view illustrating a container;

DETAILED DESCRIPTION OF THE PREFERRED EMBODIMENT(S) OF THE PRESENT INVENTION

Figure 1:
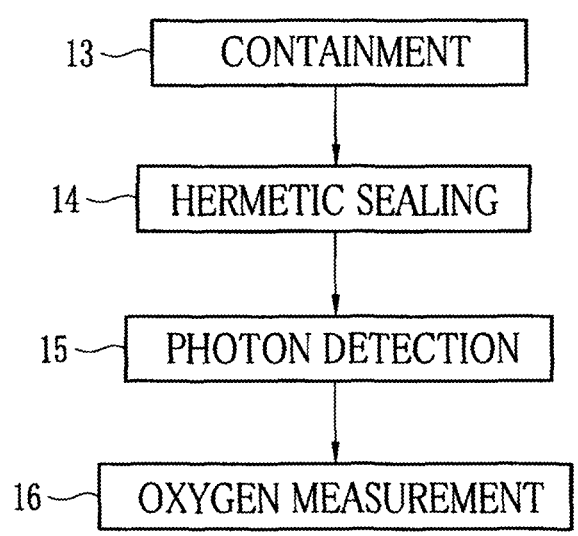
FIG. 1 is a flow chart illustrating an oxygen permeability measuring method.

In FIG. 1, an oxygen permeability measuring method includes steps of containment 13, hermetic sealing 14, photon detection 15, and oxygen measurement 16. In the containment 13, a container which has an opening and filled with inert gas is provided with a chemiluminescent compound (CL compound) which emits light upon oxidation. In the hermetic sealing 14, an oxygen barrier film as a sample material for measurement is used for closing the opening in the container hermetically. In the photon detection 15, photons emitted from the chemiluminescent compound are detected. In the oxygen measurement 16, an amount of the oxygen entered in the container after permeation through the oxygen barrier film is measured.

Figure 2:
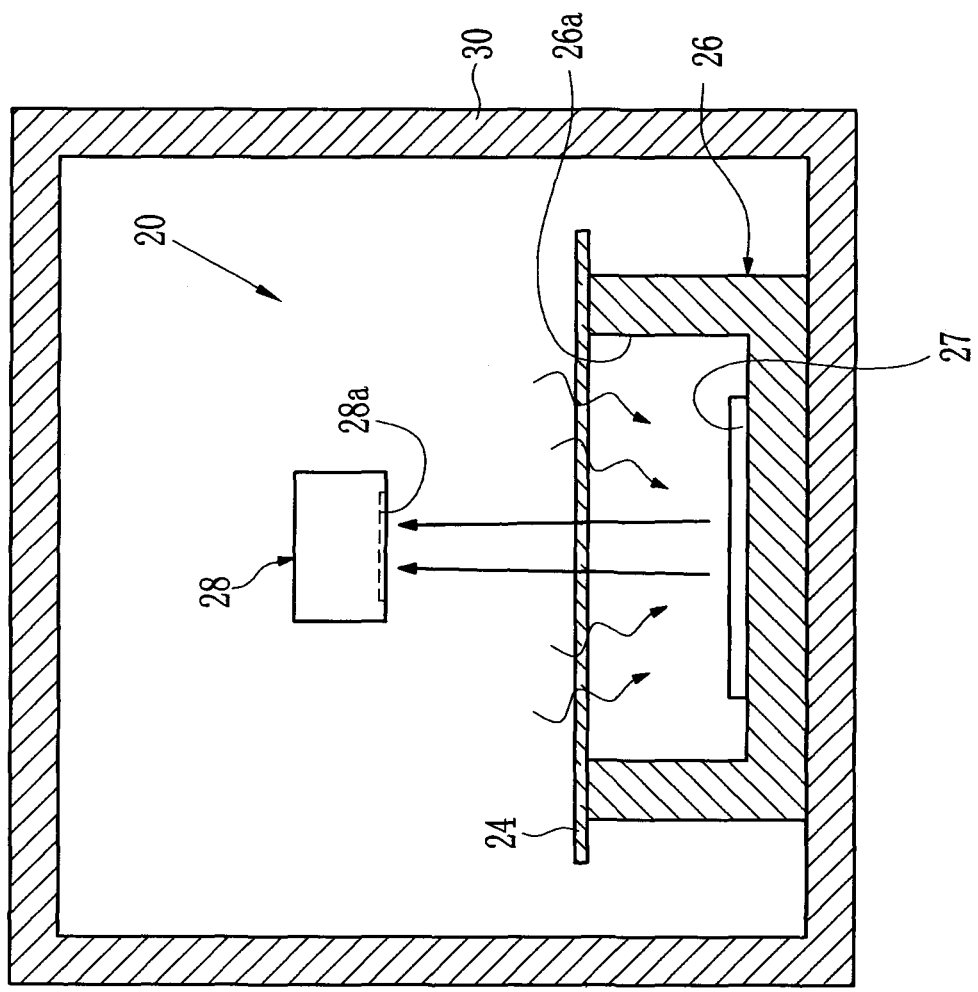
FIG. 2 is a cross section illustrating one preferred oxygen permeability measuring apparatus.

In FIG. 2, an oxygen permeability measuring apparatus 20 for the oxygen permeability measuring method is illustrated. The amount of oxygen permeated through an oxygen barrier film 24 is measured. The oxygen permeability measuring apparatus 20 includes a container 26, a chemiluminescer 27 or chemical sensor formed from a chemiluminescent compound, and a photon counter 28 or photon detector. An opening 26a is formed to open in the container 26. The photon counter 28 detects photons emitted by the chemiluminescer 27. In a dark room 30, the oxygen permeability measuring apparatus 20 is placed.

The container 26 has a wall having low oxygen permeability than that of the oxygen barrier film 24. For example, the wall has oxygen permeability of glass or the like. The opening 26a may be formed in any size or shape, and should be formed in a closable form with the oxygen barrier film 24 so as to keep the container 26 sealed tightly.

The container 26 is filled with inert gas. Examples of inert gas include rare gas, and other gas such as nitrogen as a low reactive gas.

The chemiluminescer 27 is disposed inside the container 26 under the opening 26a. The chemiluminescer 27 includes a base sheet of filter paper or the like, and a chemiluminescent compound provided in the base sheet by impregnation or in other conditions.

The chemiluminescent compound of the invention is a compound emitting photons by reaction upon oxygen, for example, a compound having a double bond of substitution of an electron providing group, fat having an unsaturated bond, and the like. Among those, a compound having a double bond of substitution of an electron providing group is specifically preferable in view of strongly emitted light. A preferable example of the compound is expressed in Formula 1 as follows.

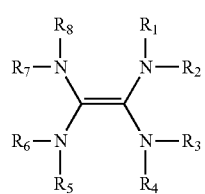

Formula 1

In Formula 1, R1-R8 denote alkyl groups independent of one another. Those alkyl groups may be bonded to one another to form a ring structure.

The alkyl groups R1-R8 have 1-18 carbon atoms, preferably 1-8 carbon atoms, and have a linear, branched or ring structure. The alkyl groups R1-R8 may contain a substitution group. Examples of the substitution group include an alkoxy group (preferably with 1-4 carbon atoms, for example, methoxy, ethoxy and 2-methyl propoxy); acyl group (preferably with 2-4 carbon atoms, for example, acetyl, butyloyl and pivaloyl); acyloxy group (preferably with 2-4 carbon atoms, for example, acetoxy, butyloyl oxy and pivaloyl oxy); and halogen atom (for example, F, Cl, Br and I). Alkyl groups R1-R8 of ring structures are any one of 4 to 7-membered rings, preferably 5 or 6-membered ring. Rings defined by a bond between the alkyl groups R1-R8 are any one of 4 to 8-membered rings, preferably 5 or 6-membered ring.

A specifically preferable compound among those expressed by Formula 1 is one in which the alkyl groups R1-R8 are unsubstituted alkyl groups independent of one another and having one or two carbon atoms. Furthermore, it is preferable that among the alkyl groups having one or two carbon atoms, R2 and R3 are bonded together to constitute 5 or 6-membered ring, and R6 and R7 are bonded together to constitute 5 or 6-membered ring.

Among the various examples expressed by Formula 1, the most preferable compound is one in which R1-R8 are methyl groups as alkyl groups. Specific examples of the compounds according to Formula 1 are hereinafter referred to as Compounds I-16. Note that Formulas 2 and 3 are structurally included in examples of Formula 1. Compounds I-5 are examples of tetrakis(dialkylamino)ethylene. Of course, the feature of the invention is not limited to those examples.

TABLE 1

| Symbols | Compound 1 | Compound 2 | Compound 3 | Compound 4 |
|---|---|---|---|---|
| R1 | $CH_3$ | $CH_3$ | $C_2H_5$ | $C_8H_{17}$ |
| R2 | $CH_3$ | $C_2H_5$ | $C_2H_5$ | $CH_3$ |
| R3 | $CH_3$ | $CH_3$ | $C_2H_5$ | $C_8H_{17}$ |
| R4 | $CH_3$ | $C_2H_5$ | $C_2H_5$ | $CH_3$ |
| R5 | $CH_3$ | $CH_3$ | $C_2H_5$ | $C_8H_{17}$ |
| R6 | $CH_3$ | $C_2H_5$ | $C_2H_5$ | $CH_3$ |
| R7 | $CH_3$ | $CH_3$ | $C_2H_5$ | $C_8H_{17}$ |
| R8 | $CH_3$ | $C_2H_5$ | $C_2H_5$ | $CH_3$ |

| Symbols | Compound 5 | Compound 6 | Compound 7 | Compound 8 |
|---|---|---|---|---|
| R1 | $C_{18}H_{37}$ | $C_2H_4OCH_3$ | $C_2H_4OCOCH_3$ | Cyclohexyl group |
| R2 | $CH_3$ | $C_2H_4OCH_3$ | $C_2H_4OCOCH_3$ | $CH_3$ |
| R3 | $C_{18}H_{37}$ | $C_2H_4OCH_3$ | $C_2H_4OCOCH_3$ | Cyclohexyl group |
| R4 | $CH_3$ | $C_2H_4OCH_3$ | $C_2H_4OCOCH_3$ | $CH_3$ |
| R5 | $C_{18}H_{37}$ | $C_2H_4OCH_3$ | $C_2H_4OCOCH_3$ | Cyclohexyl group |
| R6 | $CH_3$ | $C_2H_4OCH_3$ | $C_2H_4OCOCH_3$ | $CH_3$ |
| R7 | $C_{18}H_{37}$ | $C_2H_4OCH_3$ | $C_2H_4OCOCH_3$ | Cyclohexyl group |
| R8 | $CH_3$ | $C_2H_4OCH_3$ | $C_2H_4OCOCH_3$ | $CH_3$ |

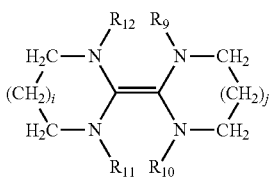

Formula 2

TABLE 2

| Symbols | Compound 9 | Compound 10 | Compound 11 | Compound 12 |
|---|---|---|---|---|
| i | 0 | 0 | 0 | 0 |
| j | 0 | 0 | 0 | 0 |
| R9 | $CH_3$ | $C_2H_5$ | $C_2H_5$ | $n\text{-}C_3H_7$ |
| R10 | $CH_3$ | $C_2H_5$ | $C_2H_5$ | $n\text{-}C_3H_7$ |
| R11 | $CH_3$ | $C_2H_5$ | $CH_3$ | $n\text{-}C_3H_7$ |
| R12 | $CH_3$ | $C_2H_5$ | $CH_3$ | $n\text{-}C_3H_7$ |

| Symbols | Compound 13 | Compound 14 | Compound 15 |
|---|---|---|---|
| i | 0 | 0 | 1 |
| j | 0 | 0 | 1 |
| R9 | $n\text{-}C_4H_9$ | $n\text{-}C_6H_{13}$ | $CH_3$ |
| R10 | $n\text{-}C_4H_9$ | $n\text{-}C_6H_{13}$ | $CH_3$ |
| R11 | $n\text{-}C_4H_9$ | $n\text{-}C_6H_{13}$ | $CH_3$ |
| R12 | $n\text{-}C_4H_9$ | $n\text{-}C_6H_{13}$ | $CH_3$ |

Formula 3 is a structure of Compound 16.

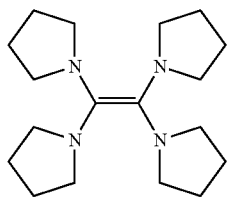

Formula 3

Compounds expressed by Formula 1 can be synthesized according to known methods. Compounds I-8 can be synthesized according to methods disclosed in:

R. L. Pruett, J. T. Barr, K. E. Rapp, C. T. Bahner, J. D. Gibson and R. H. Lafferty, Jr., *J. Am. Chem. Soc.* 72 (1950), pp. 3646-3650;

N. Wiberg and J. W. Buchler, *Z. Naturforsch. B* 196, pp. 5-8 (1964).

Compounds 9-16 can be synthesized according to methods disclosed in:

H. E. Winberg, J. E. Carnahan, D. D. Coffman, and M. Brown, *J. Am. Chem. Soc.* 87 (1965) pp. 2055-2056.

A process of luminescence according to the invention is described with an example of reaction between the tetrakis (dimethylamino)ethylene (Compound 1) and oxygen. When the tetrakis(dimethylamino)ethylene reacts on oxygen, dioxetane of Formula 4 is produced as an intermediate product before two molecules of tetramethyl urea (see Formulas 5 and 6) are produced. The tetramethylurea of Formula 6 is in an excited state. While the tetramethyl urea of Formula 6 transfers to a ground state, photons are emitted with energy corresponding to an energy difference between the excited state and the ground state. According to the description in H. E. Winberg, J. R. Downing and D. D. Coffman, *J. Am. Chem. Soc.* 87, pp. 2054-2055 (1965), the quantum yield of the reaction is $3\times10^{-4}$. Therefore, the photons are emitted at a reaction rate κ of 2.5-3.4 photons per 10,000 molecules of oxygen.

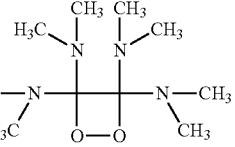

Formula 4

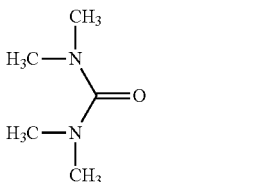

Formula 5

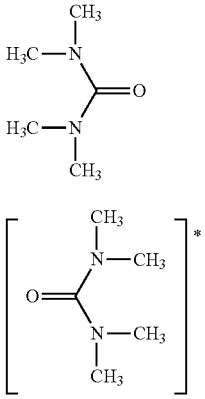

Formula 6

The photon counter 28 includes a photomultiplier tube and a counter module. An entrance opening 28a is formed in the photomultiplier tube for receiving entry of photons. The counter module counts the number of photons entered through the entrance opening 28a according to a value of a current output by the photomultiplier tube. The photon counter 28 is disposed outside the container 26 to oppose the entrance opening 28a to the opening 26a. A quantum efficiency Qe of the photomultiplier tube is preferably 1-20% with changes in the conversion wavelength of photons.

The oxygen barrier film 24 has optical transmittance. A preferable range of an oxygen permeation rate of the oxygen barrier film 24 is from $10^{-2}$ to $10^{-6}$ cc/m²·day·atm.

A sequence for measuring an oxygen permeation rate of the oxygen barrier film 24 with the oxygen permeability measuring apparatus 20 is described, according to the use of filter paper containing tetrakis(dimethylamino)ethylene for the chemiluminescer 27.

[Containment and Hermetic Sealing]

At first, a glove box is filled with inert gas. The container 26, a fluid tight bottle and the oxygen barrier film 24 are placed in the glove box, the fluid tight bottle containing the chemiluminescer 27. Inside the glove box, the chemiluminescer 27 is taken out of the fluid tight bottle, and disposed within the container 26. Then the oxygen barrier film 24 is attached to the container 26 to close the opening 26a. Thus, the container 26 is sealed in a state of substituting internal air in the container 26 having the chemiluminescer 27 with the inert gas. The container 26 is transferred into a transport trunk case in the glove box, and transported into the dark room 30. Note that the transport trunk case is also filled with inert gas.

Oxygen-containing gas, such as air, is filled in the dark room 30. An inner pressure of the container 26 may be equal to that of the dark room 30 or may be lower than the dark room 30. In relation to environmental conditions of the container 26, various factors, such as humidity, temperature and the like of the container 26 are not limited in a manner suitable for reaction of a chemiluminescent compound.

[Photon Detection]

In the dark room 30, the container 26 is removed from the transport trunk case. The container 26 is so positioned as to oppose the opening 26a to the entrance opening 28a of the photon counter 28 to be disposed in the dark room 30. In the dark room 30, oxygen is permeated through the oxygen barrier film 24. The oxygen contacts the chemiluminescer 27 disposed in the container 26. Reaction occurs between the tetrakis(dimethylamino)ethylene in the chemiluminescer 27 and the oxygen to emit photons. The photons travel to enter the entrance opening 28a of the photon counter 28. In response to this, the photomultiplier tube generates a pulse current of a predetermined level corresponding to photons.

[Oxygen Measurement]

The counter module reads information of a current and a number of pulses output by the photomultiplier tube. The counter module determines the number of photons having entered the entrance opening 28a according to the current and the number of pulses being read. Furthermore, the number M (per second) of oxygen molecules permeated through the oxygen barrier film 24 is determined according to the photon number and the reaction rate κ.

An oxygen permeation rate T ($cc/m^2 \cdot day \cdot atm$) is defined by Equation 1.

$$T = M \cdot 3600 \cdot 24 / (S \cdot Qe \cdot K \cdot \kappa \cdot A)$$ Equation 1

Note that S is an area of the opening 26a, Qe is a quantum yield of the photon counter, K is a photon collection efficiency, and A is the number of oxygen molecules per unit volume and determined in considering the temperature and pressure of the measurement. The photon collection efficiency K is a ratio of photons entering the entrance opening 28a among those emitted by the chemiluminescer 27, and is specifically determined from a three dimensional angle of the entrance opening 28a of the photomultiplier tube in the chemiluminescer 27. It is further possible to determine the photon collection efficiency K by considering various parameters, which may include areas and forms of the opening 26a and the chemiluminescer 27, positions of the chemiluminescer 27 and the entrance opening 28a, and inner reflection of the container 26.

Thus, the measurement of the oxygen permeability can be performed at higher sensitivity than before, because the number of photons is detected after oxidation for the purpose of measuring the oxygen permeability of the oxygen barrier film 24. Even the oxygen barrier film 24 of a small oxygen permeability can be measured in contrast with the prior art.

Figure 3:
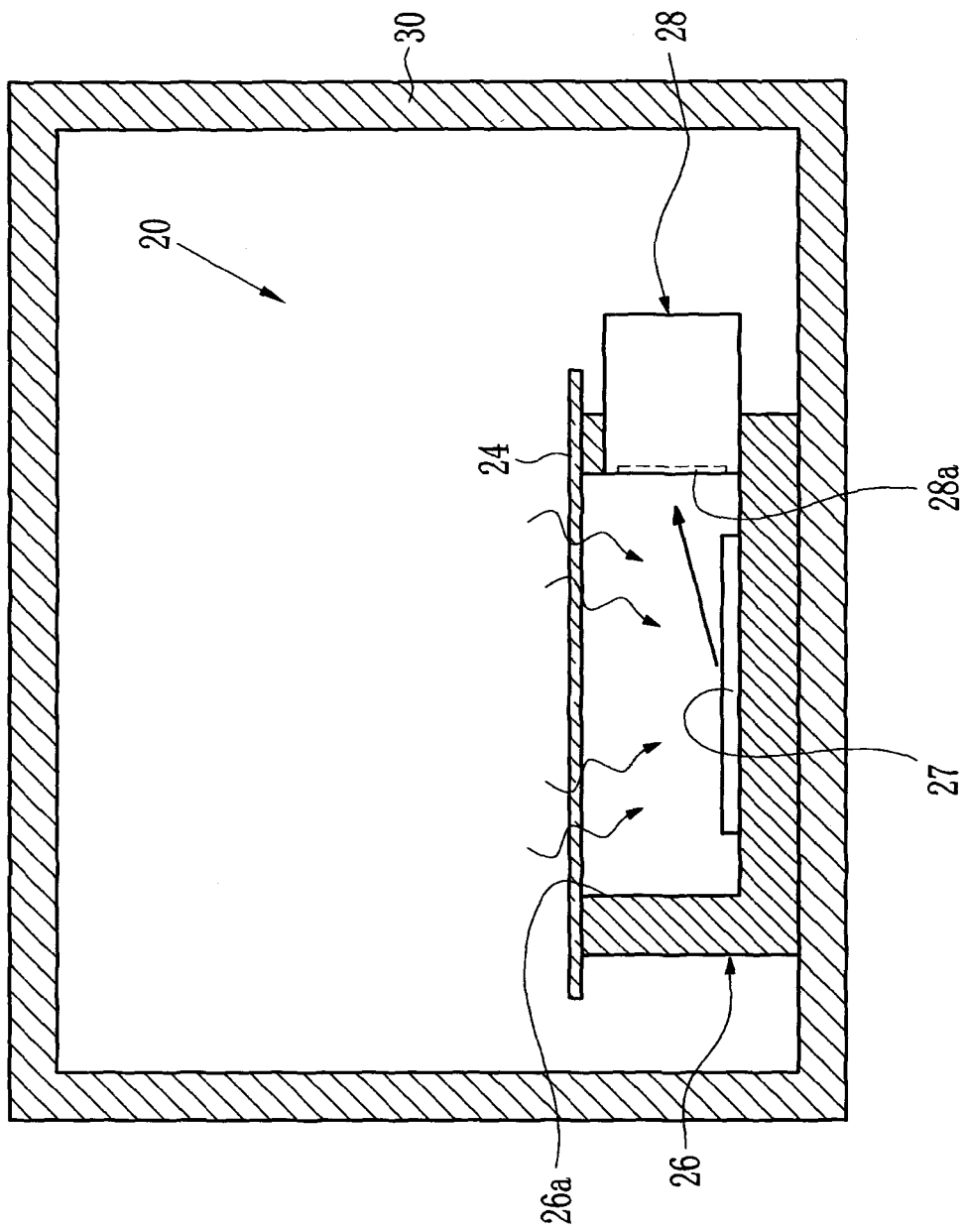
FIG. 3 is a cross section illustrating another preferred oxygen permeability measuring apparatus in which a photon counter is directed laterally.

In the above embodiment, the oxygen barrier film 24 with optical transmittance is used. However, the oxygen barrier film 24 may have low optical transmittance or no optical transmittance. For this construction, photons may be detected through the container 26, or the photon counter 28 may be disposed inside the container 26. Also, the photon counter 28 may be so disposed as to position the entrance opening 28a inside the container 26 as illustrated in FIG. 3. Note that the photon collection efficiency K is previously determined in a suitable manner.

In the embodiment, the container 26 is removed from the transport trunk case within the dark room 30. Instead of this, the photon counter 28 can be positioned inside or outside the glove box in the dark room 30 before the internal gas in the glove box can be substituted with the atmosphere.

Figure 4:
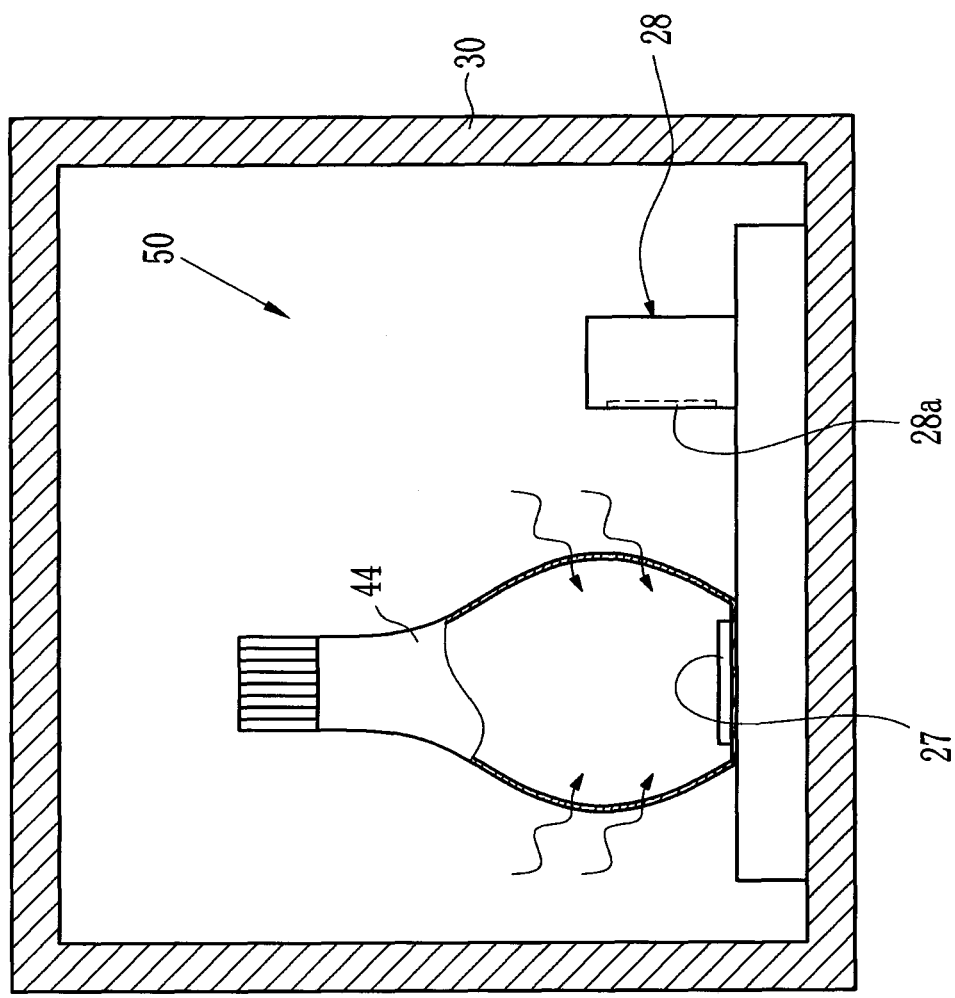
FIG. 4 is a cross section illustrating one preferred oxygen permeability measuring apparatus in which an oxygen barrier container is used.

In the above embodiment, the oxygen permeation rate of the oxygen barrier film 24 is measured. However, an oxygen permeation rate of an oxygen barrier container 44 of FIG. 4 can be measured according to the invention. An oxygen permeability measuring apparatus 50 for the oxygen permeability of the oxygen barrier container 44 as a container bag includes the chemiluminescer 27 and the photon counter 28. The oxygen barrier container 44 is filled with inert gas before the chemiluminescer 27 is placed in the oxygen barrier container 44. Tasks of the containment 13, the hermetic sealing 14, the photon detection 15 and the oxygen measurement 16 are performed in the same manner as the above embodiment. A preferable range of the oxygen permeation rate of the oxygen barrier container 44 is equal to that of the oxygen barrier film 24.

The operation of measuring oxygen permeability of the oxygen barrier container 44 with the oxygen permeability measuring apparatus 50 is described now.

A glove box is filled with inert gas. The oxygen barrier container 44 as a container bag and a fluid tight bottle containing the chemiluminescent compound for the chemiluminescer 27 are placed in the glove box. In the glove box, the chemiluminescent compound is taken out of the fluid tight bottle and positioned in the oxygen barrier container 44. Then the oxygen barrier container 44 is sealed in a state substituted with inert gas. The oxygen barrier container 44 is transferred to a transport trunk case inside the glove box, and transported into the dark room 30.

[Containment and Hermetic Sealing]

In the dark room 30, the oxygen barrier container 44 is taken out of the transport trunk case. The oxygen barrier container 44 is disposed in front of the entrance opening 28a of the photon counter 28. In the dark room 30, oxygen is permeated through the oxygen barrier container 44. The oxygen contacts the chemiluminescer 27 disposed in the oxygen barrier container 44. Reaction occurs between the tetrakis(dimethylamino)ethylene in the chemiluminescer 27 and the oxygen to emit photons.

[Photon Detection and Oxygen Measurement]

The photons travel to enter the entrance opening 28a of the photon counter 28. In response, the photomultiplier tube outputs a pulse current of a predetermined amount. The counter module reads the current and the pulse number output by the photomultiplier tube, and detects the number of photons having entered the entrance opening 28a. Furthermore, the number M (per second) of oxygen molecules permeated through the oxygen barrier container 44 is determined according to the number of the photons and a reaction rate κ.

Figure 5A:
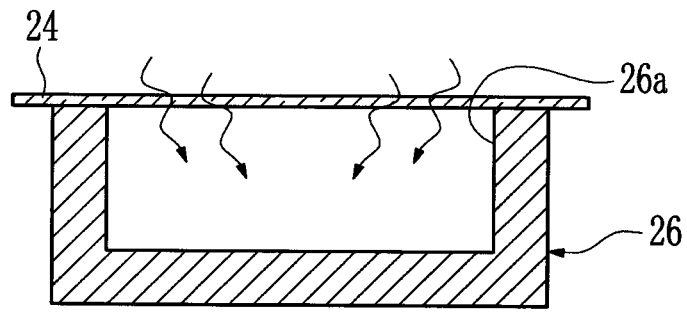
FIG. 5A is a cross section illustrating one preferred oxygen permeability measuring system.
Figure 5B:
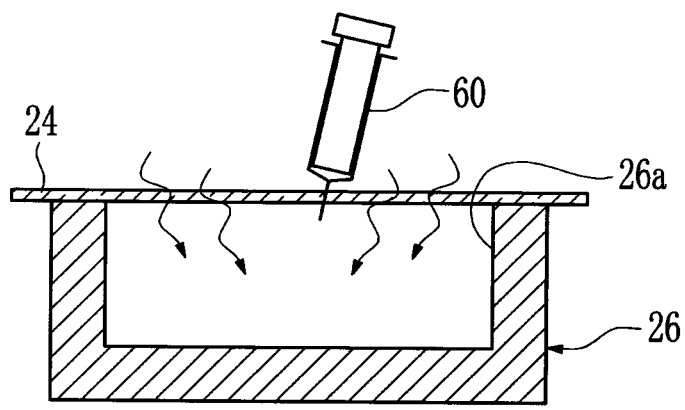
FIG. 5B is a cross section illustrating an intermediate step in a sequence in operation of the oxygen permeability measuring system.
Figure 5C:
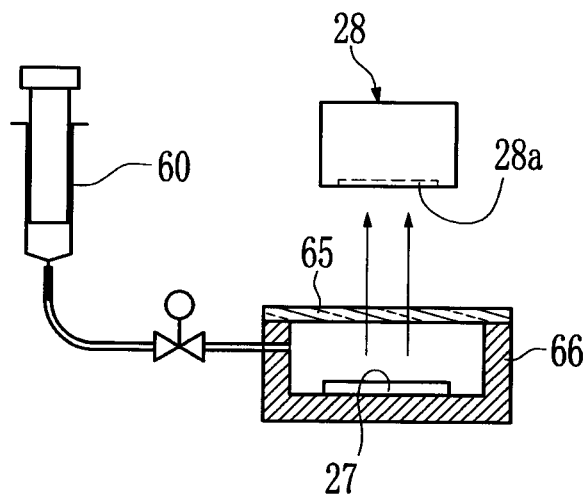
FIG. 5C is an explanatory view in a side elevation illustrating a test container for use in the oxygen permeability measuring system.

FIGS. 5A-5C illustrate another preferred method. The container 26 is exposed in the atmosphere of oxygen-containing gas, for example air, in a tightly closed state with the oxygen barrier film 24 after substitution of internal air with inert gas. See FIG. 5A. When time t1 elapses, oxygen of a predetermined amount is permeated through the oxygen barrier film 24 to enter the container 26. A syringe 60 is used to draw gas from the container 26 by suction. See FIG. 5B. There is a test container 66 which is tightly closed by use of a glass lid 65. The removed gas is introduced by the syringe 60 into the test container 66. See FIG. 5C. As the chemiluminescer 27 is contained in the test container 66, the chemiluminescer 27 emits photons upon contact with oxygen. It is possible with the photon counter 28 to determine an amount of oxygen or number m of oxygen molecules permeated through the oxygen barrier film 24 because the number of photons emitted by the chemiluminescer 27 depends on the amount of oxygen permeated through the oxygen barrier film 24. The oxygen permeation rate T is defined by Equation 2.

$$T = m / (S \cdot Qe \cdot K \cdot \kappa \cdot A \cdot t1)$$ Equation 2

In the measurement, time t1 is defined from the start of the introduction of gas until an end of light emission. m is a count of photons in this period. T is an average oxygen permeation rate at time t1.

Note that the oxygen barrier container 44 can be used in place of the oxygen barrier film 24 and the container 26 in FIG. 5A.

The structure of the container 26 is not limited. In FIG. 6, one example is illustrated, in which a recess 61 is formed in a lower surface 26b of the container 26. A chemiluminescent compound (CL compound) 62 is filled in the recess 61 at the center of the lower surface 26b to provide a chemiluminescer or chemical sensor. See FIG. 7. For high sensitivity for detecting oxygen, it is preferable that a ratio S26a/S62 is equal to or more than 1, where S26a is an area of the opening 26a closed by the oxygen barrier film 24, and S62 is an area of the chemiluminescent compound 62. The recess 61 can be formed in any of various shapes including a square shape, rectangular quadrilateral shape, circular shape, elliptic shape and the like.

EXAMPLE

In an experiment, oxygen permeability of the oxygen barrier film 24 was measured by the oxygen permeability measuring apparatus 20 of FIG. 2. An inner dimension of the container 26 was 0.012×0.017×0.0007 (meter). The chemiluminescent compound was tetrakis(dimethylamino)ethylene. The opening area S26a was $2.04 \times 10^{-4}$ m$^2$ (=0.012× 0.017 meter). The entirety of the lower surface of the container 26 was covered with tetrakis(dimethylamino)ethylene. The photon collection efficiency K was 0.025. The quantum efficiency Qe of the photon counter was 0.04. The reaction rate κ was 0.0003. The number A of oxygen molecules per volume in the condition of the temperature and air pressure at the measurement was $2.4 \times 10^{19}$ molecules per cc. As a result of measuring the oxygen barrier film, the number of photons upon the lapse of four (4) days from the start of the measurement was 10 per second in a condition of subtracting background noise. Thus, the oxygen permeation rate was measured as $5.9 \times 10^{-4}$ cc/m$^2$·day·atm. Note that measurement of the same oxygen barrier film (with the oxygen permeability rate of $5.9 \times 10^{-4}$ cc/m$^2$·day·atm) according to the method disclosed in the document JP-A 54-130091 may require approximately 1,300 times as long a duration as the present embodiment.

For tens of photons generated every second, $3.3 \times 10^7$ oxygen molecules per second reacted upon tetrakis(dimethylamino)ethylene according to effect of Qe, κ and K. A volume of the container 26 in use was $1.43 \times 10^{-7}$ m$^3$. The number of gas molecules in the container 26 was $3.48 \times 10^{18}$ under one atmosphere pressure and room temperature. Oxygen molecules instantaneously reacted on tetrakis(dimethylamino)ethylene in the small space of the container 26. Oxygen of such an amount was provided every second through the oxygen barrier film. In a condition of balancing the entry and disappearance of oxygen molecules, a maximum of the oxygen density in the container 26 was determined as:

$$3.3 \times 10^7 / (3.48 \times 10^{12}) \approx 0.9 \times 10^{-11}$$

It follows that the sensitivity of detecting oxygen in the oxygen permeability measuring apparatus was 10 ppt.

Figure 7:
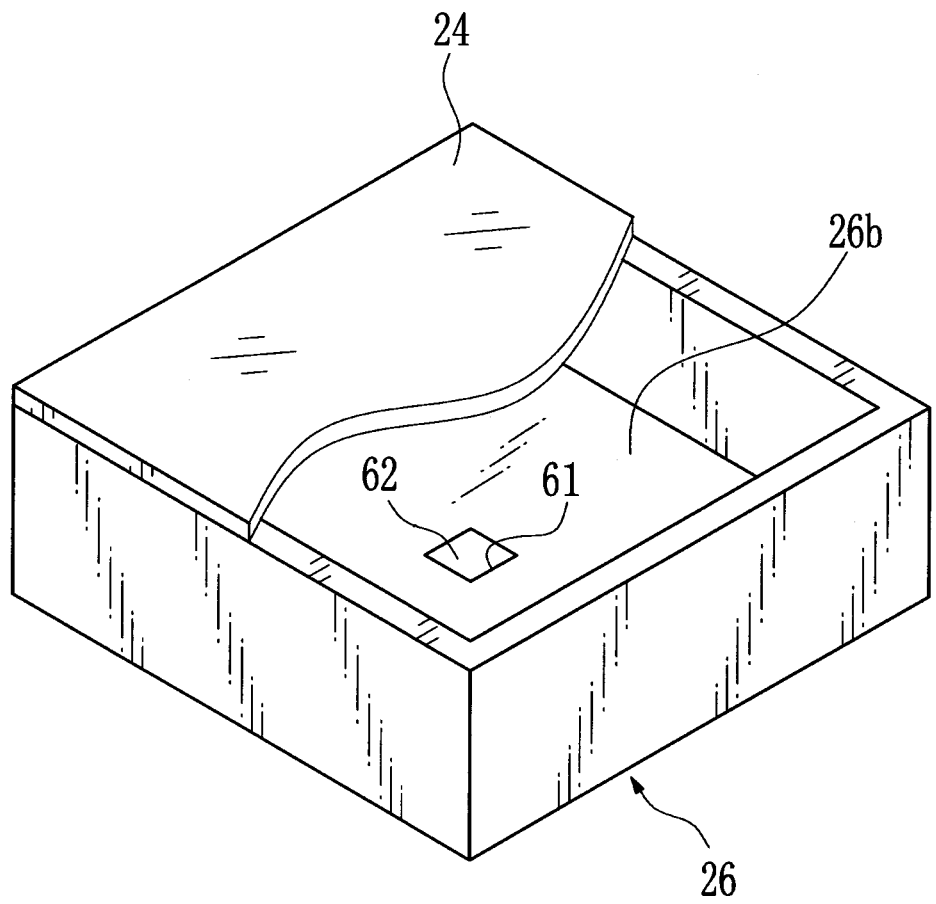
FIG. 7 is a perspective view, partially broken, illustrating the container.

Note that the counted number of photons can be increased without changing the photon collection efficiency K, the reaction rate κ or the quantum efficiency Qe of the photon counter, because of enlargement of the opening area S26a. If opening area S26a of the container 26 in FIGS. 6 and 7 is 100 times as large as the area S62 of the chemiluminescent compound 62, the amount of the signal becomes 100 times larger. As a result, a range of the measurement is $10^{-6}$ cc/m$^2$·day·atm. It is concluded that the sensitivity of detecting oxygen is equal to or less than 1 ppt.

Figure 8:
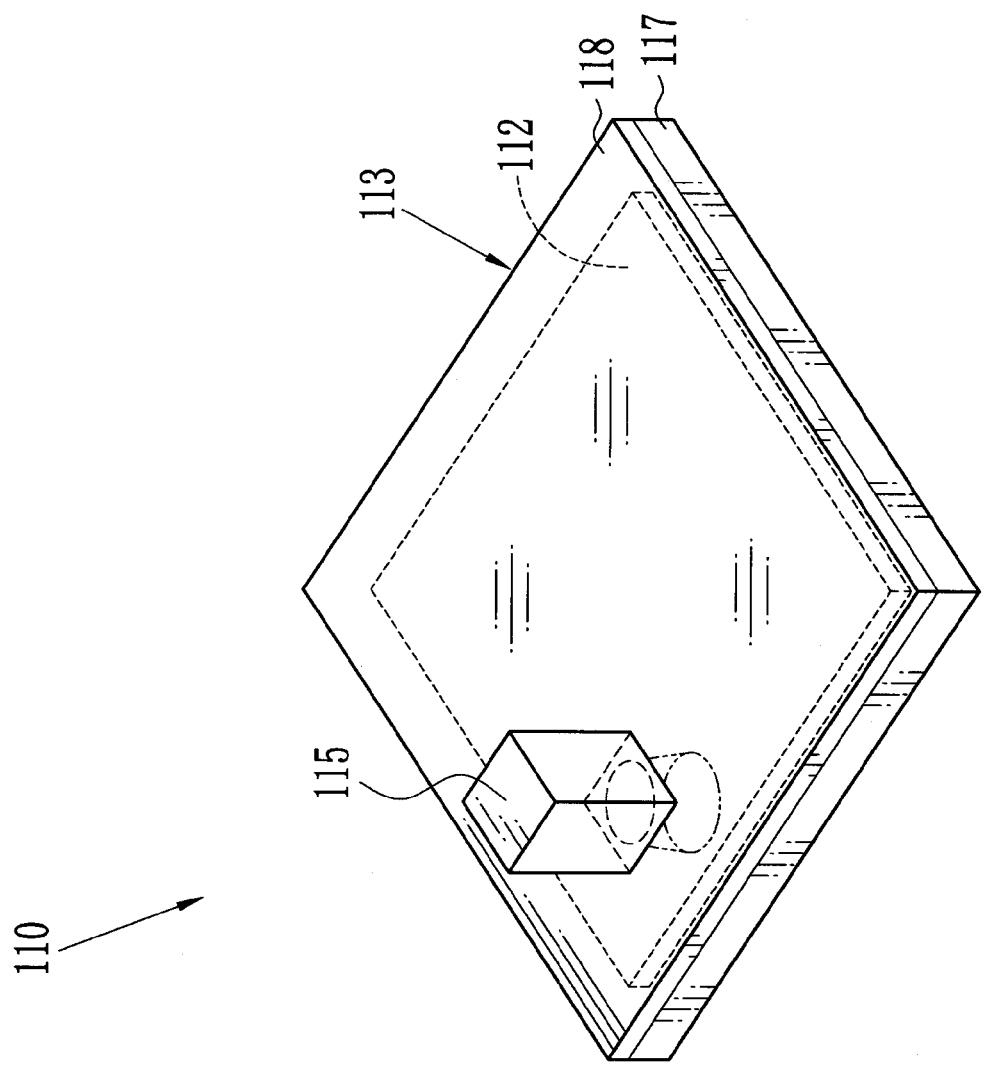
FIG. 8 is a perspective view illustrating a defect inspection apparatus of the invention.

In FIG. 8, a defect inspection apparatus 110 of the invention is illustrated. The defect inspection apparatus 110 includes a hermetic container 113 and a photon counter 115 or photon detector. A chemiluminescent compound (CL compound) 112 is contained in the hermetic container 113. The photon counter 115 is disposed near to the hermetic container 113. The hermetic container 113 has a wall with an oxygen barrier property.

Figure 9:
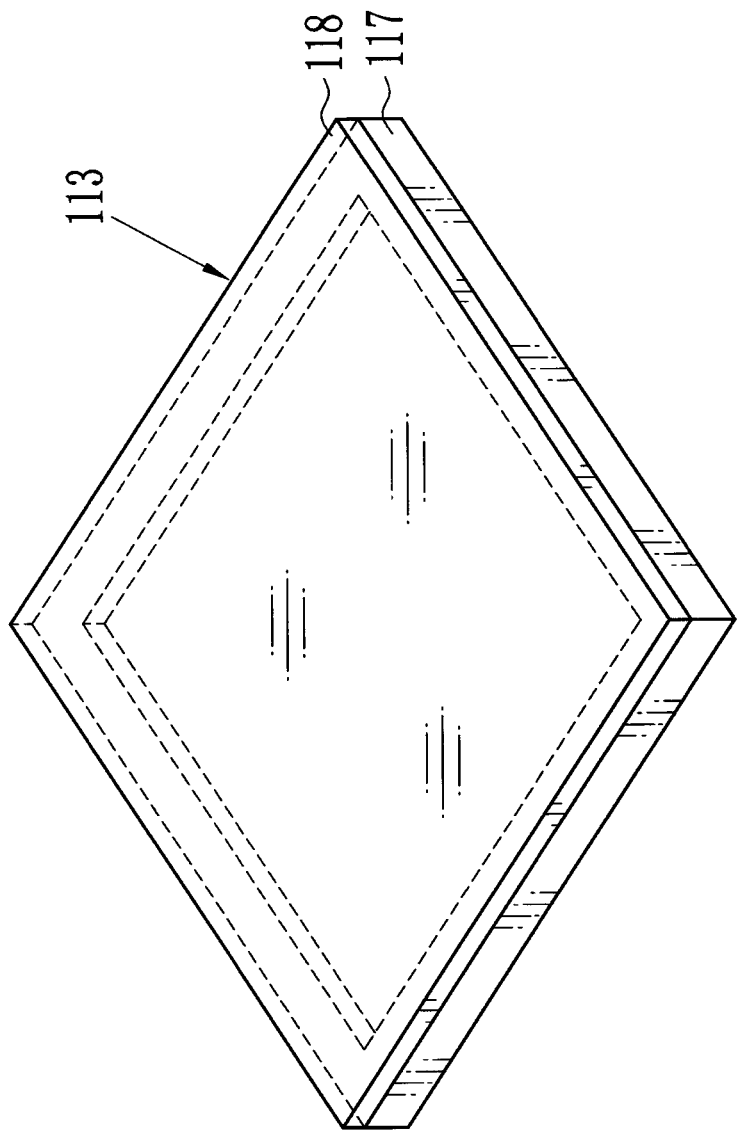
FIG. 9 is a perspective view illustrating a hermetic container in the defect inspection apparatus.
Figure 10:
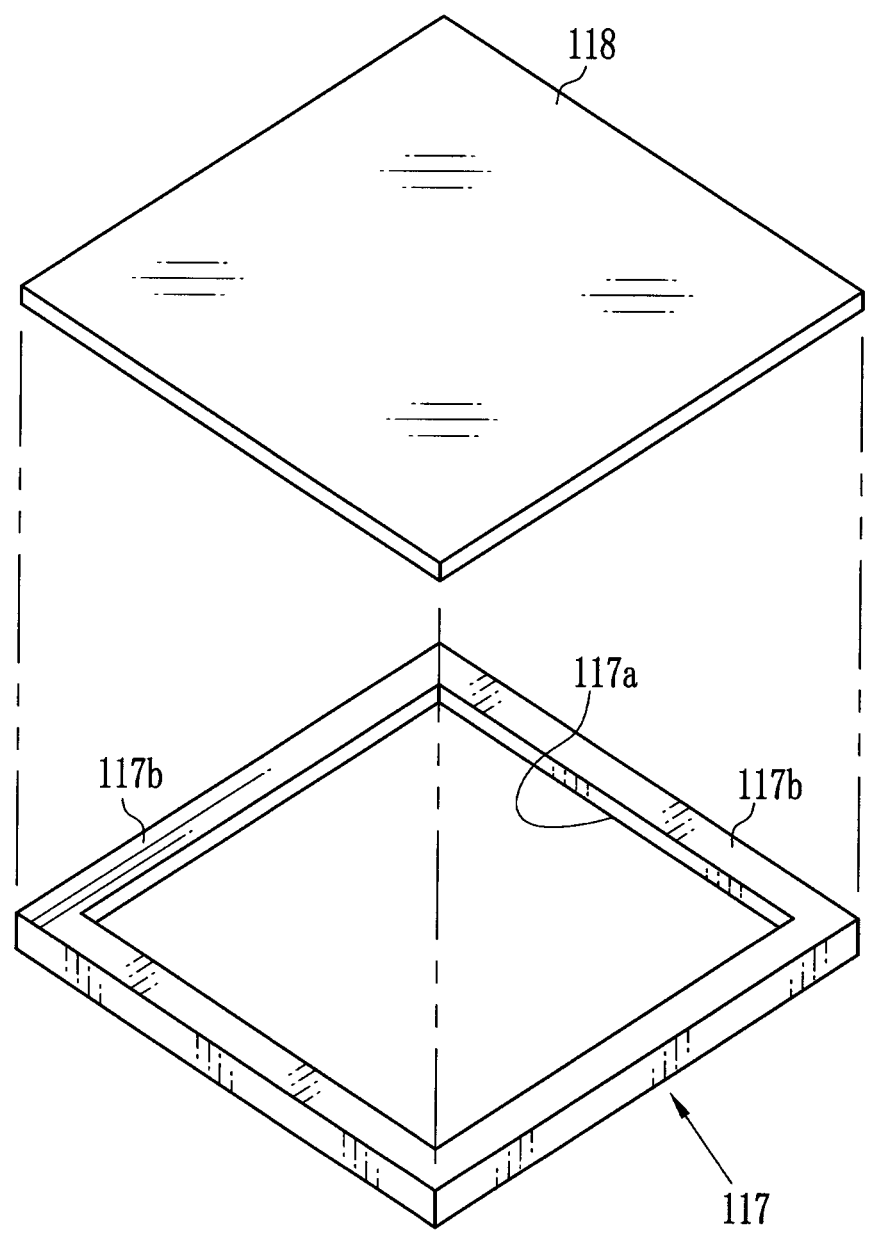
FIG. 10 is a perspective view illustrating the hermetic container.

In FIGS. 9 and 10, the hermetic container 113 includes a container body 117 and oxygen barrier film 118. The container body 117 contains the chemiluminescent compound 112. The oxygen barrier film 118 is a sample material of the defect inspection. The container body 117 includes an opening 117a and a support surface 117b, which is disposed around the opening 117a and supports the oxygen barrier film 118.

The oxygen barrier film 118 has optical transmittance. A range of an oxygen permeation rate of the oxygen barrier film 118 is from $10^{-2}$ to $10^{-6}$ cc/m$^2$·day·atm, and preferably from $10^{-2}$ to $10^{-3}$ cc/m$^2$·day·atm.

Figure 11:
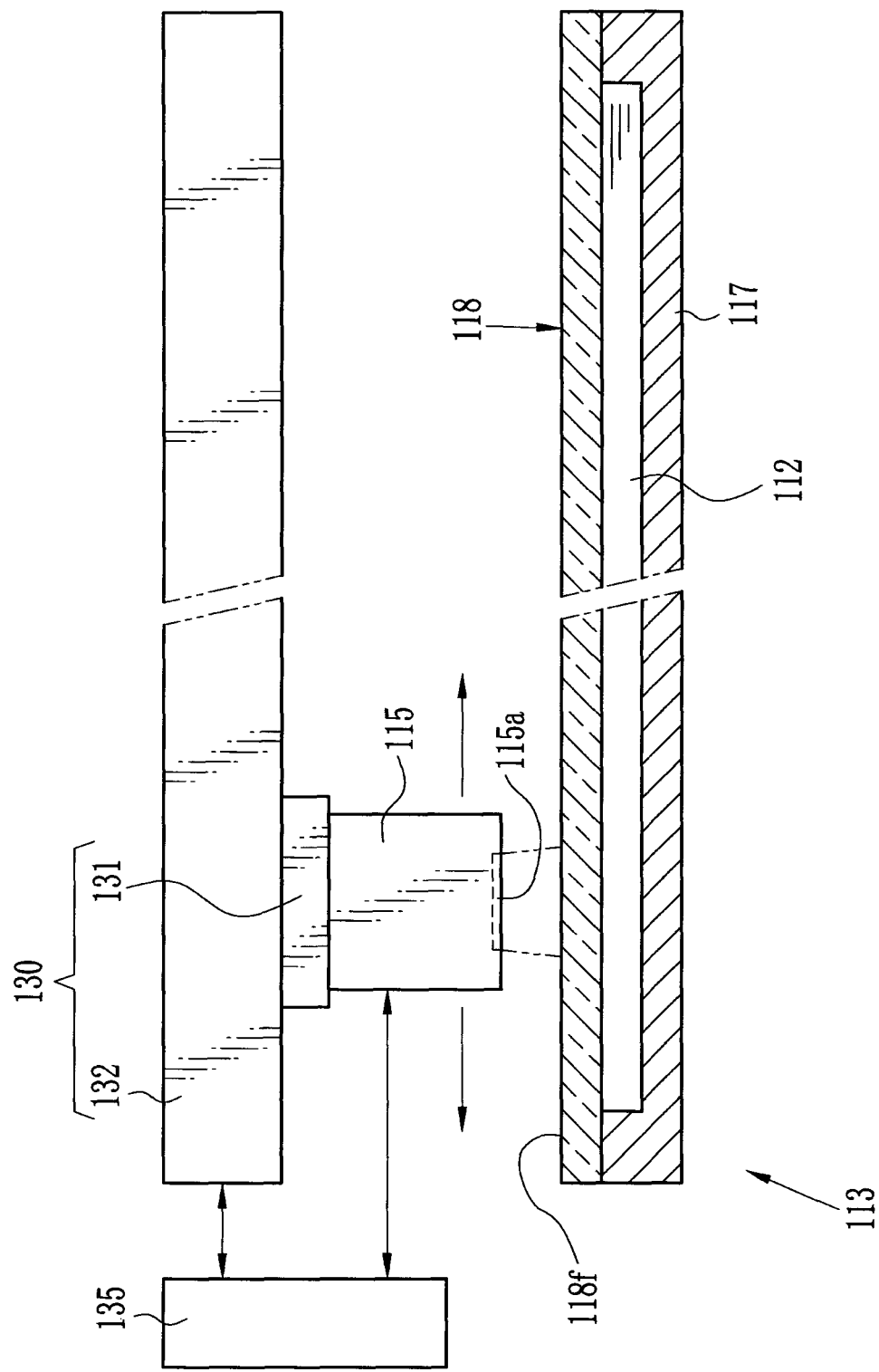
FIG. 11 is an explanatory view in a side elevation illustrating the defect inspection apparatus.

When the oxygen barrier film 118 is placed and attached on the container body 117 to close the opening 117a, the chemiluminescent compound in the container body 117 is sealed as illustrated in FIG. 11. The chemiluminescent compound 112 is enclosed inside the hermetic container 113.

Various methods can be used for providing a chemiluminescent compound in the container body 117. For example, a blade may be used for spreading the chemiluminescent compound after ejecting droplets of the chemiluminescent compound. A sheet coating apparatus may be used for coating the chemiluminescent compound by moving a movable part parallel to a horizontally installed base plate, the movable part being one of a blade, wire bar, hopper and the like. Also, a spin coating apparatus may be used for rotating while a base plate is held horizontally.

To seal the chemiluminescent compound 112 in the container body 117, sealing material is used, such as ethylene vinyl acetate copolymer (EVA). The support surface 117b of the container body 117 is coated with EVA before the oxygen barrier film 118 is attached with tight contact. A width of coating of the sealing material is 1 cm or more. Note that the oxygen barrier film 118 is attached tightly by removing gas (inert gas in the glove box) from between the oxygen barrier film 118 and the chemiluminescent compound 112. If the region of the defect inspection is a portion of the lower surface of the container body 117, there is no problem with gas remaining outside the region of the defect inspection between the oxygen barrier film 118 and the chemiluminescent compound.

In FIG. 11, a moving device 130 supports the photon counter 115 by attachment. The moving device 130 includes a movable holder 131 and a driving mechanism 132 for moving the holder 131 in a moving direction. The photon counter 115 is kept movable because attached to the holder 131.

An entrance opening 115a is included in the photon counter 115 disposed outside the hermetic container 113. The photon counter 115 is positioned to oppose the entrance opening 115a to the oxygen barrier film 118.

A controller 135 in connection with the photon counter 115 reads the number of photons counted by the counter module. The controller 135 reads a position of the holder 131 from the driving mechanism 132. Furthermore, the controller 135 drives the driving mechanism 132 according to route information stored in an internal memory. The holder 131 is controlled by the controller 135 and moves on a path from a start point to an endpoint. The internal memory stores information of the start point, endpoint and path between those.

The operation of defect inspection of the oxygen barrier film 118 in the defect inspection apparatus 110 is described now.

At first, a glove box is filled with inert gas. The container body 117, a fluid tight bottle and the oxygen barrier film 118 are placed in the glove box, the fluid tight bottle containing the chemiluminescent compound. See FIG. 10.

In the glove box, a chemiluminescent compound is drawn from the fluid tight bottle, and is supplied to apply a coating to the container body 117. The oxygen barrier film 118 is attached to the container body 117 to close the opening 117a. Thus, the chemiluminescent compound 112 in the container body 117 is sealed. The chemiluminescer is formed inside the hermetic container 113 as illustrated in FIG. 11. The hermetic container 113 is placed in a transport trunk case and carried into a dark room.

The moving device 130 is disposed in the dark room. The photon counter 115 is secured to the holder 131. In the dark room, the hermetic container 113 is taken out of the transport trunk case. The hermetic container 113 is so positioned as to oppose the entrance opening 115a of the photon counter 115 to the oxygen barrier film 118 at a distance equal to or less than 1 cm.

The controller 135 sets the photon counter 115 at the start point. Then the controller 135 reads information of holder coordinates of a position of the holder 131 from the driving mechanism 132. The controller 135 checks whether the holder coordinates coincide with coordinates of the endpoint stored in the internal memory. If the holder coordinates do not coincide with those of the end point, then the controller 135 drives the holder 131 to move on a path of path information stored in the internal memory. The controller 135 moves the holder 131 until the holder coordinates become equal to the coordinates of the end point. Thus, the photon counter 115 moves on a film surface 118f of the oxygen barrier film 118 on the path extending to the end point.

The oxygen in the dark room permeates through the oxygen barrier film 118 and contacts the chemiluminescent compound in the hermetic container 113. A portion of a defect emits light brightly at an initial step of the measurement, because of quick permeation of oxygen and its high amount.

The controller 135 by way of a comparison unit reads the oxygen molecule number M (per second) from the photon counter 115. Then the controller 135 writes oxygen amount information (oxygen measurement information) to the internal memory, the oxygen amount information including holder coordinates and the oxygen molecule number M associated therewith. After this, the controller 135 checks whether the oxygen molecule number M is larger than the threshold N previously stored in the internal memory. Note that the threshold N may be determined according to oxygen permeability required for the oxygen barrier film 118 as a sample material of defect inspection.

If it is found that M>N, then the controller 135 by way of a determining device assigns defect data to the oxygen amount information for the oxygen molecule number M, and writes succeeding oxygen amount information to the internal memory. If it is found that M<N or M=N, then the controller 135 writes succeeding oxygen amount information to the internal memory without assigning defect data to the oxygen amount information.

In the presence of defects on the oxygen barrier film 118, the oxygen molecule number M at the defects is higher than the threshold N. Thus, presence and position of defects of the oxygen barrier film 118 can be checked according to oxygen amount information stored in the internal memory in the controller 135. It is possible to inspect defects on the oxygen barrier film 118 at a higher speed than before, because the defects are checked by use of the number of photons emitted upon the oxidation.

In the above embodiment, the entirety of the lower surface of the container body 117 is covered by the chemiluminescent compound. However, only an area inside the container body 117 for inspection can be covered with the chemiluminescent compound without extension in the entirety of the lower surface.

In the embodiment, the container body 117 includes the opening 117a and the support surface 117b. However, a flat plate can be used in place of the container body 117. The chemiluminescent compound can be placed on the flat plate. Then a region around the chemiluminescent compound is coated with sealing material before the oxygen barrier film 118 can be attached to the flat plate by tight contact.

In the above embodiment, the oxygen barrier film 118 has optical transmittance. However, the oxygen barrier film 118 may have low optical transmittance or no optical transmittance. For this structure, the container body 117 preferably can be transparent with optical transmittance. The photon counter 115 may be disposed near to a rear surface of the container body 117 to detect photons through the container body 117.

Figure 12:
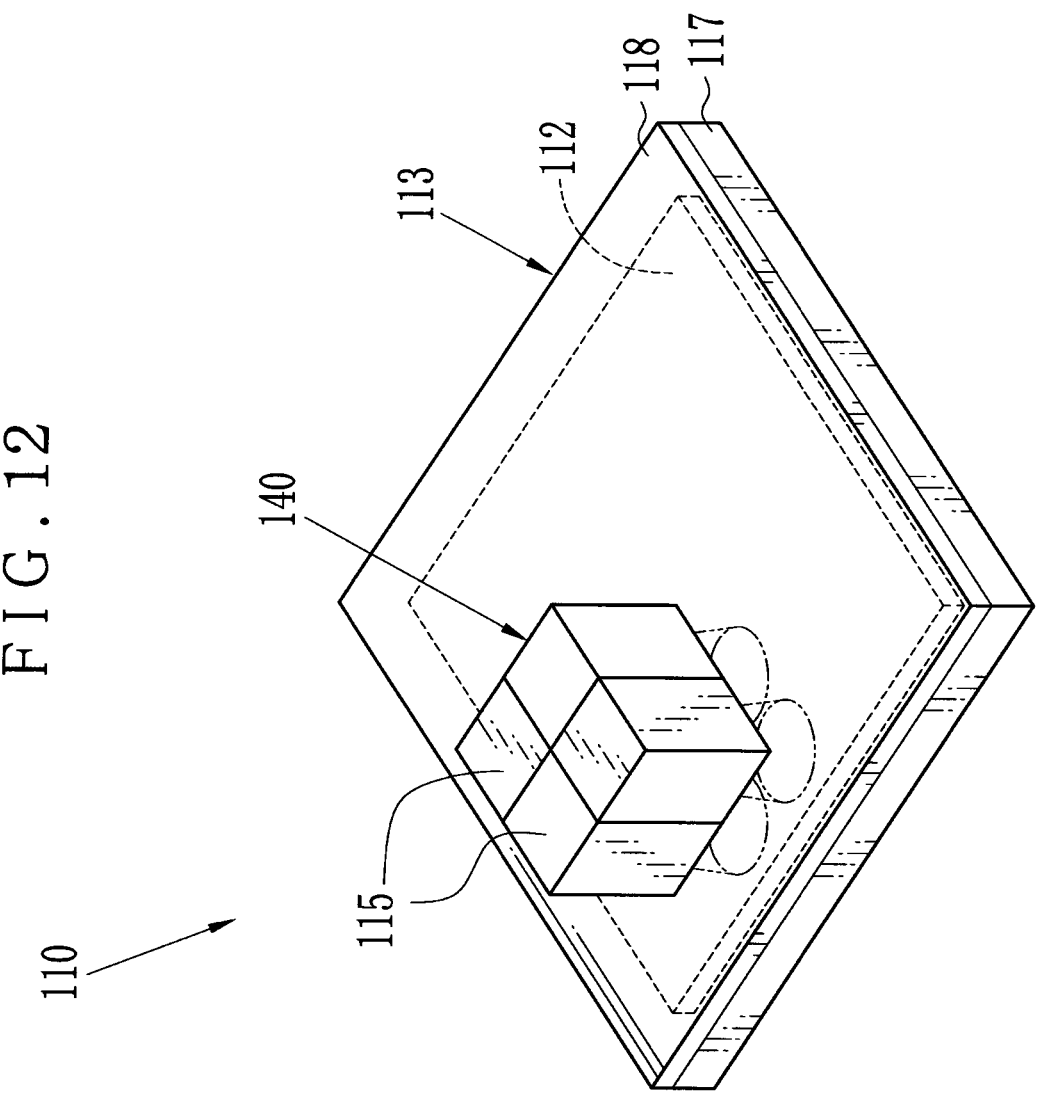
FIG. 12 is a perspective view illustrating one preferred defect inspection apparatus having a photon counter array.
Figure 13:
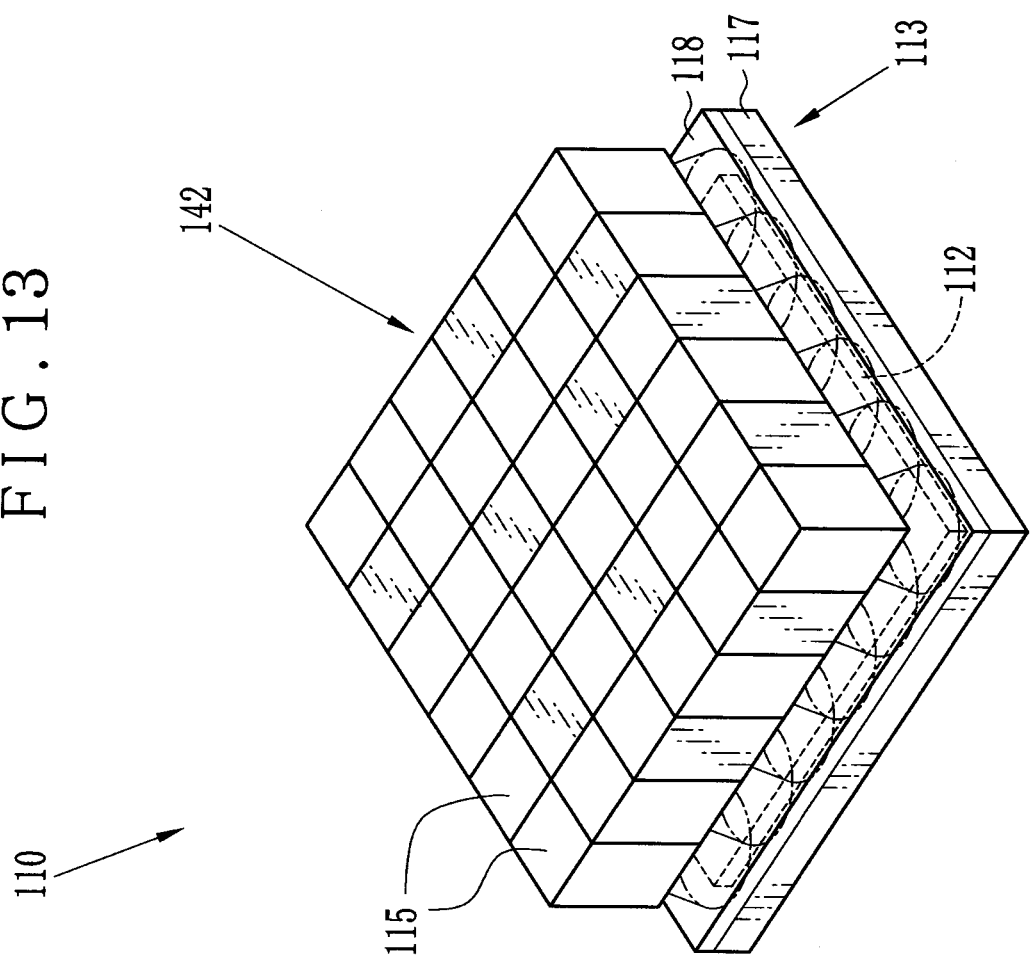
FIG. 13 is a perspective view illustrating another preferred defect inspection apparatus having a photon counter array of a larger form.

In the above embodiment, the photon counter 115 is single. In FIGS. 12 and 13, other preferred embodiments are illustrated, in which photon counter arrays 140 and 142 of photon counters are used. In FIG. 12, the photon counter array 140 has a plurality of the photon counters 115 arranged two-dimensionally. In FIG. 13, the photon counter array 142 has a plurality of the photon counters 115 arranged to cover the entirety of the oxygen barrier film 118. This makes it possible to remove the use of the moving device 130 in FIG. 11.

Figure 14:
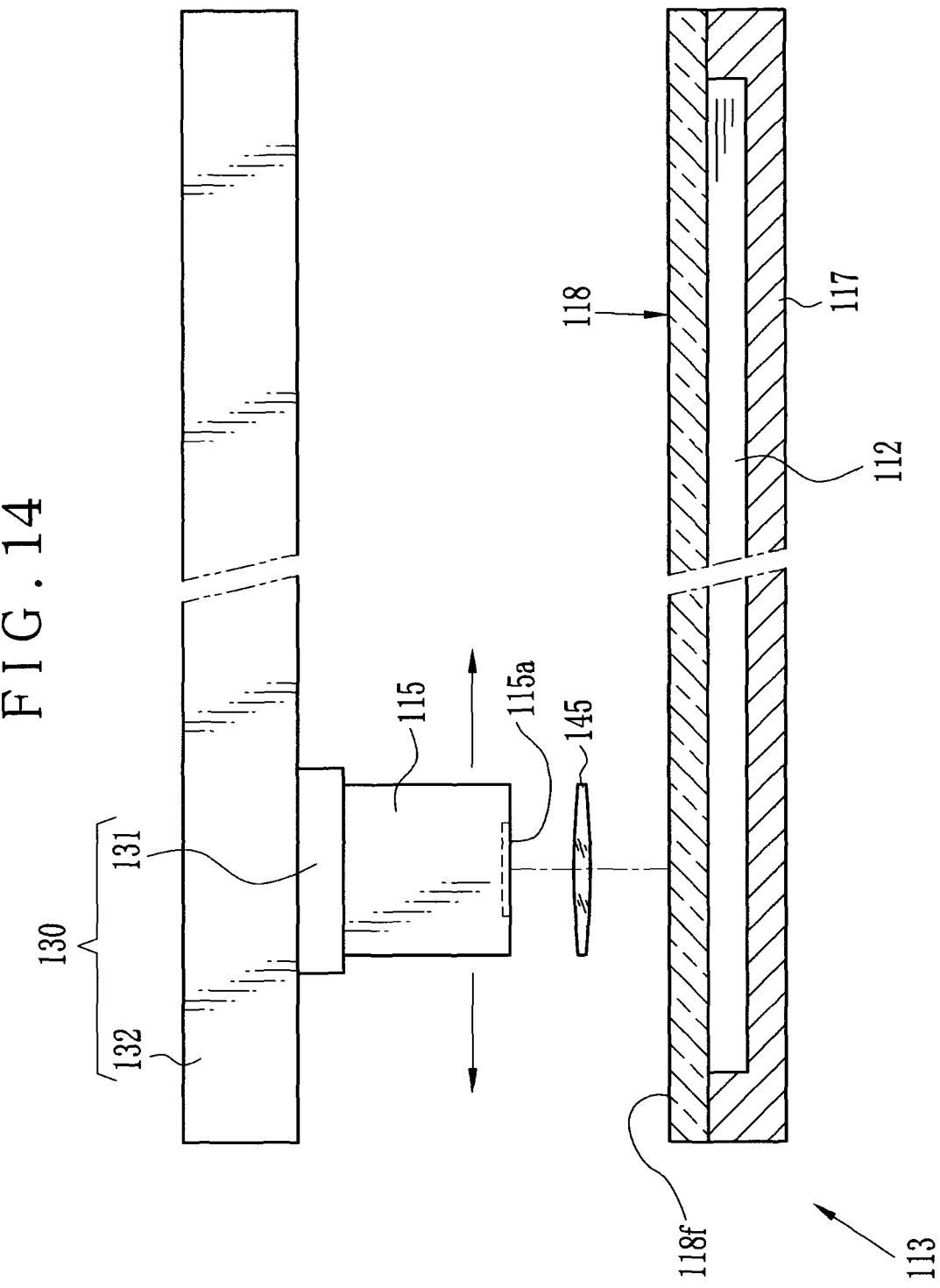
FIG. 14 is an explanatory view in a side elevation illustrating one preferred defect inspection apparatus having a condensing lens.

In FIG. 14, a further preferred embodiment is illustrated, in which a condensing lens 145 is disposed between the photon counter 115 and the oxygen barrier film 118. The condensing lens 145 is preferably disposed so that its focal point is positioned at the entrance opening 115a. This is effective in raising precision of a position of defects on the oxygen barrier film 118.

In the above embodiment, the photomultiplier tube is used. However, a photon counter of the invention may be constituted by light sensing elements having an ultrahigh resolution, such as an CCD image sensor having an image intensifier. In the use of the CCD image sensor, the measurement is according to measurement of an integration type with storage of photons.

EXAMPLE

Defect inspection was conducted for an oxygen barrier material by use of the defect inspection apparatus 110 in FIG. 8. The oxygen barrier material included a base film having fine pores, and a plate of metal overlaid on the base film. The oxygen permeation rate of a portion of the oxygen barrier material having the fine pores was 20 $cc/m^2 \cdot day \cdot atm$ (which was considerably large and indicated presence of a defect). The number of photons detected when four (4) hours elapsed after placement of the defect inspection apparatus 110 in the dark room was measured. The measured number was 10 per second in a larger region on the oxygen barrier material, but was 77 per second in a predetermined region other than the larger region. The predetermined region with the result 77 per second was found to coincide with the portion having the fine pores. Thus, it was found that fine defects could be detected exactly even in a short time according to the invention.

Although the present invention has been fully described by way of the preferred embodiments thereof with reference to the accompanying drawings, various changes and modifications will be apparent to those having skill in this field. Therefore, unless otherwise these changes and modifications depart from the scope of the present invention, they should be construed as included therein.

What is claimed is:

1. An oxygen permeability measuring apparatus for measuring an oxygen permeation rate of an oxygen barrier film, comprising:
    a container charged with inert gas and sealed hermetically, at least partially by use of the oxygen barrier film;
    a chemiluminescent compound, contained in said container, configured to emit light by oxidation with oxygen; and
    a photon detector configured to:
        receive said photons emitted by said chemiluminescent compound through an opening of the photon detector positioned inside said container, and
        detect said photons emitted by said chemiluminescent compound, so as to determine an amount of oxygen permeated through said oxygen barrier film into said container.

2. The oxygen permeability measuring apparatus as defined in claim 1, wherein said container comprises:
    a container body; and
    an opening, formed in said container body, and closed hermetically by said oxygen barrier film.

3. The oxygen permeability measuring apparatus as defined in claim 1, wherein said container is a container bag constituted by said oxygen barrier film.

4. The oxygen permeability measuring apparatus as defined in claim 3, wherein said photon detector is disposed inside or outside said container.

5. The oxygen permeability measuring apparatus as defined in claim 1, wherein said oxygen barrier film has an oxygen permeation rate equal to or less than $10^{-2}$ cc/m$^2$·day·atm.

6. The oxygen permeability measuring apparatus as defined in claim 1, wherein said chemiluminescent compound includes a compound according to a formula of:

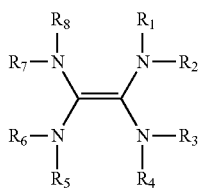

where R1-R8 denote alkyl groups identical to or different from each other.

7. The oxygen permeability measuring apparatus as defined in claim 6, wherein said chemiluminescent compound includes tetrakis(dimethylamino)ethylene.

8. The oxygen permeability measuring apparatus as defined in claim 1, wherein said photon detector comprises a photomultiplier tube.

9. An oxygen permeability measuring method comprising:
    disposing a container charged with inert gas in a dark room;
    containing a chemiluminescent compound in the container charged with inert gas, the chemiluminescent compound being configured to emit light by oxidation with oxygen;
    permeating oxygen-containing gas through an oxygen barrier film to contact the chemiluminescent compound in the container, thereby causing the chemiluminescent compound to emit light;
    using a photon detector with an opening for receiving photons positioned inside the container to detect an amount of photons emitted by the chemiluminescent compound; and
    determining an amount of oxygen permeated through the oxygen barrier film according to the amount of photons emitted by the chemiluminescent compound.

10. The oxygen permeability measuring method as defined in claim 9, wherein the container is hermetically sealed, at least partially, by the oxygen barrier film.

11. The oxygen permeability measuring method as defined in claim 10, wherein the container comprises:
    a container body; and
    an opening, formed in the container body, and closed hermetically by the oxygen barrier film.

12. The oxygen permeability measuring method as defined in claim 10, wherein the container is a container bag constituted by the oxygen barrier film.

13. The oxygen permeability measuring method as defined in claim 9, further comprising:
    before said permeating, hermetically sealing a gas container with the oxygen barrier film in charging said gas container with inert gas; and
    after said permeating, drawing the permeated oxygen-containing gas from the gas container to introduce the permeated oxygen-containing gas into the container.

14. A defect inspection apparatus for an oxygen barrier material, comprising:
    a hermetic container constituted, at least partially, by the oxygen barrier material;
    a chemiluminescent compound, contained in said container, configured to emit light by oxidation with oxygen;
    a photon counter configured to detect a number M of photons emitted by said chemiluminescent compound;
    a comparison unit configured to check whether said number M is more than a threshold N;
    a moving device configured to move said photon counter along said oxygen barrier material; and
    a determining device configured to determine a detection position of said photon counter upon detecting said number M, if said comparison unit determines that M>N.

15. The defect inspection apparatus as defined in claim 14, wherein said photon counter comprises plural photon counters disposed in a photon counter array.

16. The defect inspection apparatus as defined in claim 15, wherein said photon counter array is disposed along a surface of said oxygen barrier material.

17. The defect inspection apparatus as defined in claim 14, further comprising a condensing lens for light condensing of said photons emitted by said chemiluminescent compound to said photon counter.

18. The defect inspection apparatus as defined in claim 14, wherein said oxygen barrier material has an inner surface fitted on said chemiluminescent compound, and seals said container.

19. The defect inspection apparatus as defined in claim 18, wherein said container comprises:
- a container body; and
- an opening, formed in said container body, and closed hermetically by said oxygen barrier material.

20. The defect inspection apparatus as defined in claim 14, wherein said chemiluminescent compound includes tetrakis(dimethylamino)ethylene.

21. The defect inspection apparatus as defined in claim 14, wherein said photon counter comprises a photomultiplier tube.

22. The defect inspection apparatus as defined in claim 14, wherein a condensing lens is arranged between said photon counter and said oxygen barrier material.

23. A defect inspection method for an oxygen barrier material, comprising:
- containing a chemiluminescent compound configured to emit light by oxidation with oxygen in a hermetic container, the container being constituted, at least partially, by the oxygen barrier material;
- exposing the container containing the chemiluminescent compound to oxygen in a dark room;
- wherein said exposing step comprises:
- moving a photon counter along the oxygen barrier material to detect plural positions along the oxygen barrier a number M of photons emitted by the chemiluminescent compound by use of a photon counter contained in the container;
- checking whether the number M is more than a threshold N; and
- determining a detection position of the photon counter upon detecting the number M, if M>N.

24. An oxygen permeability measuring apparatus for measuring an oxygen permeation rate of an oxygen barrier film, comprising:
- a container bag constituted by the oxygen barrier film, charged with inert gas and sealed hermetically, at least partially by use of the oxygen barrier film;
- a chemiluminescent compound, contained in said container bag, configured to emit light by oxidation with oxygen; and
- a photon detector configured to detect said photons emitted by said chemiluminescent compound, so as to determine an amount of oxygen permeated through said oxygen barrier film into said container bag.

25. An oxygen permeability measuring method comprising:
- disposing a container bag constituted by an oxygen barrier film, charged with inert gas in a dark room;
- containing a chemiluminescent compound in the container bag charged with inert gas, the chemiluminescent compound being configured to emit light by oxidation with oxygen;
- permeating oxygen-containing gas through the oxygen barrier film to contact the chemiluminescent compound in the container bag, thereby causing the chemiluminescent compound to emit light;
- detecting an amount of photons emitted by the chemiluminescent compound; and
- determining an amount of oxygen permeated through the oxygen barrier film according to the amount of photons emitted by the chemiluminescent compound.

* * * * *